US010350149B2

(12) United States Patent
Aubrun et al.

(10) Patent No.: US 10,350,149 B2
(45) Date of Patent: *Jul. 16, 2019

(54) ANHYDROUS ANTIPERSPIRANT COMPOSITION IN AEROSOL FORM COMPRISING AN ANTIPERSPIRANT ACTIVE AGENT AND A WATER-INSOLUBLE FILM-FORMING BLOCK ETHYLENIC POLYMER

(71) Applicant: L'OREAL, Paris (FR)

(72) Inventors: Odile Aubrun, Antony (FR); Xavier Jalenques, Gennevilliers (FR); Laurence Sebillotte-Arnaud, l'Hay les Roses (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/105,653

(22) PCT Filed: Dec. 18, 2014

(86) PCT No.: PCT/EP2014/078385
§ 371 (c)(1),
(2) Date: Jun. 17, 2016

(87) PCT Pub. No.: WO2015/091742
PCT Pub. Date: Jun. 25, 2015

(65) Prior Publication Data
US 2017/0007510 A1  Jan. 12, 2017

(30) Foreign Application Priority Data

Dec. 19, 2013 (FR) ..................... 13 63008

(51) Int. Cl.
| | | |
|---|---|---|
| *A61K 8/04* | (2006.01) | |
| *A61K 8/26* | (2006.01) | |
| *A61K 8/28* | (2006.01) | |
| *A61K 8/81* | (2006.01) | |
| *A61K 8/31* | (2006.01) | |
| *A61K 8/90* | (2006.01) | |
| *A61Q 15/00* | (2006.01) | |
| *A61K 8/891* | (2006.01) | |
| *B65D 83/28* | (2006.01) | |
| *B65D 83/14* | (2006.01) | |

(52) U.S. Cl.
CPC ............ *A61K 8/046* (2013.01); *A61K 8/26* (2013.01); *A61K 8/28* (2013.01); *A61K 8/31* (2013.01); *A61K 8/8152* (2013.01); *A61K 8/891* (2013.01); *A61K 8/90* (2013.01); *A61Q 15/00* (2013.01); *B65D 83/28* (2013.01); *B65D 83/752* (2013.01); *A61K 2800/31* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 4,152,416 A * | 5/1979 | Spitzer ................. | A61K 8/046 424/45 |
| 5,002,698 A | 3/1991 | Wirth et al. | |
| 6,403,070 B1 | 6/2002 | Pataut et al. | |
| 6,649,173 B1 | 11/2003 | Arnaud et al. | |
| 2006/0115444 A1* | 6/2006 | Blin ...................... | A61K 8/26 424/70.16 |
| 2010/0183536 A1 | 7/2010 | Ansmann et al. | |
| 2010/0189665 A1 | 7/2010 | Dierker et al. | |
| 2010/0189673 A1 | 7/2010 | Jackwerth et al. | |
| 2010/0247588 A1 | 9/2010 | Hloucha et al. | |
| 2010/0311627 A1 | 12/2010 | Hloucha et al. | |
| 2011/0059032 A1 | 3/2011 | Dierker et al. | |
| 2011/0142778 A1 | 6/2011 | Hloucha et al. | |

(Continued)

FOREIGN PATENT DOCUMENTS

| | | |
|---|---|---|
| DE | 102008012457 A1 | 12/2008 |
| EP | 0804921 A1 | 11/1997 |

(Continued)

OTHER PUBLICATIONS

FR 2990854 EPO english translation, Mar. 24, 2017.*
Isododecane test data ([obtained from on-line website: http://www.isododecane.net/ETDS.htm, pp. 1-2, 2006]). (Year: 2006).*
International Search Report for PCT/EP2014/078385, dated Apr. 9, 2015.
English language abstract for FR 2990854A1 (Nov. 29, 2013).

*Primary Examiner* — Ernst V Arnold
*Assistant Examiner* — Kyung S Chang
(74) *Attorney, Agent, or Firm* — The Marbury Law Group, PLLC

(57) ABSTRACT

Anhydrous antiperspirant composition in aerosol form comprising an antiperspirant active agent and a water-insoluble film-forming block ethylenic polymer The present invention relates to an anhydrous composition in aerosol form containing: i) an oily phase comprising, in a physiologically acceptable medium: —at least one volatile oil, and —one or more antiperspirant active agents chosen from aluminum and/or zirconium salts, and —one or more water-insoluble film-forming block ethylenic polymers comprising a first block with a glass transition temperature (Tg) of greater than or equal to 85° C. and a second block with a Tg of less than or equal to 20° C., and ii) one or more propellants; the said oily phase containing less than 15% by weight and even more preferably less than 12% by weight of non-volatile polydimethylsiloxane relative to the total weight of the oils. The invention also relates to a cosmetic process for treating human perspiration, to a use of the same and to an aerosol device using the said cosmetic composition.

18 Claims, No Drawings

(56) References Cited

U.S. PATENT DOCUMENTS

2013/0149272 A1  6/2013 Hloucha et al.
2013/0280175 A1* 10/2013 Banowski .............. A61K 8/345
                                                  424/43
2017/0360658 A1  12/2017 Ferrari et al.

FOREIGN PATENT DOCUMENTS

| EP | 0847752 A1 | 6/1998 |
| EP | 1103249 A1 | 5/2001 |
| FR | 2990854 A1 | 11/2013 |
| WO | 91/18587 A1 | 12/1991 |
| WO | 98/13014 A1 | 4/1998 |
| WO | 2004/014330 A1 | 2/2004 |
| WO | 2005/074877 A1 | 8/2005 |
| WO | 2014/048648 A1 | 4/2014 |

\* cited by examiner

ANHYDROUS ANTIPERSPIRANT COMPOSITION IN AEROSOL FORM COMPRISING AN ANTIPERSPIRANT ACTIVE AGENT AND A WATER-INSOLUBLE FILM-FORMING BLOCK ETHYLENIC POLYMER

CROSS REFERENCE TO RELATED APPLICATIONS

This is a national stage application of PCT/EP2014/078385, filed internationally on Dec. 18, 2014, which claims priority to French Application No. 1363008, filed on Dec. 19, 2013, both of which are incorporated by reference herein in their entireties.

The present invention relates to an anhydrous antiperspirant composition in aerosol form comprising, in a physiologically acceptable medium, in particular a cosmetically acceptable medium, i) an oily phase comprising at least one volatile oil, one or more antiperspirant active agents chosen from aluminium and/or zirconium salts, one or more water-insoluble film-forming block ethylenic polymers, and ii) one or more propellants.

The invention also relates to a cosmetic process for treating human perspiration, and optionally the body odours associated with human perspiration, especially underarm odours, comprising the application of the said composition to a surface of the skin.

The present invention also relates to the use of the said cosmetic composition and also to an aerosol device using it.

The armpits and also certain other parts of the body are generally the site of much discomfort that may arise directly or indirectly from perspiration. This perspiration often leads to unpleasant and disagreeable sensations that are mainly due to the presence of sweat resulting from perspiration, which may, in certain cases, make the skin and clothing wet, especially in the region of the armpits or of the back, thus leaving visible marks. Finally, during its evaporation, sweat may also leave salts and/or proteins on the surface of the skin, which thus results in whitish marks on clothing. Such discomfort is noticed, including in the case of moderate perspiration.

In the cosmetic field, it is thus well known to use, in topical application, antiperspirant products containing substances that have the effect of limiting or even preventing the flow of sweat in order to overcome the problems mentioned above. These products are generally available in the form of roll-ons, sticks, aerosols or sprays.

Antiperspirant substances are generally formed from aluminium salts, such as aluminium chloride and aluminium hydroxyhalides, or complexes of aluminium and zirconium. These substances make it possible to reduce the flow of sweat.

However, cosmetic compositions based on these antiperspirant substances generally have a tendency to become transferred onto clothing, leaving unsightly, visible marks.

In order to overcome this drawback, antiperspirant compositions containing oils with a refractive index close to those of aluminium salts have been developed. The role of such oils is to reduce the whitish appearance of antiperspirant compositions when they are deposited on the skin and, consequently, to make the marks on clothing less white. The oils used are generally fatty acid esters such as isopropyl myristate.

However, such antiperspirant compositions have the drawback of giving the skin, especially on the armpits, an oily sensation that the user finds unpleasant, and do not make it possible to limit the transfer of antiperspirant products from the skin onto clothing.

There is thus a real need to use antiperspirant cosmetic compositions in aerosol form, which do not have the drawbacks mentioned above, i.e. compositions which become transferred as little as possible onto fabrics and which maintain antiperspirant efficacy.

The Applicant has thus discovered, surprisingly, that by applying to the skin an anhydrous composition in aerosol form containing an oily phase comprising one or more volatile oils, one or more antiperspirant active agents preferably chosen from aluminium and/or zirconium salts, one or more water-insoluble block ethylenic polymers as described below and one or more propellants, it is possible to minimize the transfer problems of antiperspirant compositions onto fabrics while at the same time maintaining antiperspirant efficacy; the said oily phase containing less than 15% by weight and even more preferably less than 12% by weight of non-volatile polydimethylsiloxane relative to the total weight of the oils.

Thus, the antiperspirant cosmetic composition in aerosol form in accordance with the invention leads to formulae which transfer less onto textiles, thus giving rise to fewer unsightly visible marks on clothing, especially on dark-coloured clothing, when compared with a standard antiperspirant composition or an antiperspirant composition containing oils.

In particular, the antiperspirant cosmetic composition makes it possible to significantly reduce the whitish marks on clothing, in particular on dark-coloured clothing.

Moreover, the cosmetic composition in aerosol form according to the invention maintains good antiperspirant efficacy.

Thus, the use of the water-insoluble block ethylenic polymers as described below in an antiperspirant composition based on aluminium salts makes it possible to reduce the transfer of unsightly visible marks onto clothing without harming the efficacy of the aluminium salts.

Furthermore, the water-insoluble block ethylenic polymers prove to be compatible with the aluminium salts since they do not form a macroscopically visible precipitate in the composition.

One subject of the present invention is thus especially an anhydrous composition in aerosol form, containing:
  i) an oily phase comprising, in a physiologically acceptable medium:
    one or more volatile oils,
    one or more antiperspirant active agents preferably chosen from aluminium and/or zirconium salts, and
    one or more water-insoluble film-forming block ethylenic polymers comprising a first block with a glass transition temperature (Tg) of greater than or equal to 85° C. and a second block with a Tg of less than or equal to 20° C. as defined below, and
  ii) one or more propellants;
the said oily phase preferably containing less than 15% by weight and even more preferably less than 12% by weight of non-volatile polydimethylsiloxane relative to the total weight of the oils.

The cosmetic composition according to the invention has both good transfer-resistance and antiperspirant properties.

Moreover, the present invention also relates to a cosmetic process for treating human perspiration, and optionally the body odour associated with human perspiration, which consists in applying to the surface of a human keratin material an effective amount of the cosmetic composition as described previously.

The process according to the invention is particularly advantageous for treating armpit perspiration, since the composition used does not give an unpleasant oily sensation and transfers less onto clothing, while at the same time efficiently treating perspiration.

The invention also relates to the use of the said composition for cosmetically treating human perspiration.

Other subjects, characteristics, aspects and advantages of the invention will emerge even more clearly on reading the description and the examples that follow.

For the purposes of the present invention, the term "physiologically acceptable medium" is intended to mean a medium that is suitable for the topical administration of a composition. A physiologically acceptable medium is preferentially a cosmetically or dermatologically acceptable medium, i.e. a medium that has no unpleasant colour or appearance, and that is entirely compatible with the topical administration route. In the present case, where the composition is intended for topical administration, i.e. by application at the surface of the keratin material under consideration, such a medium is considered in particular to be physiologically acceptable when it does not cause stinging, tautness or redness that is unacceptable to the user.

For the purposes of the present invention, the term "anhydrous" refers to a liquid phase with a water content of less than 5% by weight, preferably less than 2% by weight and even more preferably less than 1% by weight relative to the weight of the said composition. It should be noted that the water in question is more particularly bound water, such as the water of crystallization in salts, or traces of water absorbed by the raw materials used in the production of the compositions according to the invention.

The term "human keratin materials" means the skin (of the body, face and around the eyes), hair, eyelashes, eyebrows, bodily hair, nails, lips or mucous membranes.

The term "non-volatile polydimethylsiloxane" means a polydimethylsiloxane compound, also known as a "dimethicone", which remains on the skin or the keratin fibre at room temperature and atmospheric pressure for at least several hours, and which especially has a vapour pressure strictly less than $10^{-3}$ mmHg (0.13 Pa).

The term "polydimethylsiloxane" or "dimethicone" means any organosiloxane polymer having the following structure:

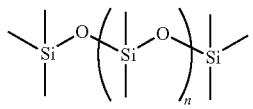

The term "final composition" means the combination of the liquid phase and of the propellant gas.

Antiperspirant Active Agent

The term "antiperspirant active agent" means a salt which, by itself, has the effect of reducing the flow of sweat, of reducing the sensation on the skin of moisture associated with human sweat and of masking human sweat.

As indicated previously, the cosmetic composition comprises one or more antiperspirant active agents preferably chosen from aluminium and/or zirconium salts.

Among the aluminium and/or zirconium salts that may be mentioned are aluminium chlorohydrate, aluminium chlorohydrex, aluminium chlorohydrex PEG, aluminium chlorohydrex PG, aluminium dichlorohydrate, aluminium dichlorohydrex PEG, aluminium dichlorohydrex PG, aluminium sesquichlorohydrate, aluminium sesquichlorohydrex PEG, aluminium sesquichlorohydrex PG, alum salts, aluminium sulfate, aluminium zirconium octachlorohydrate, aluminium zirconium pentachlorohydrate, aluminium zirconium tetrachlorohydrate, aluminium zirconium trichlorohydrate and more particularly the aluminium chlorohydrate in activated or non-activated form sold by the company Reheis under the name Microdry Aluminum Chlorohydrate® or by the company Guilini Chemie under the name Aloxicoll PF 40. Aluminium and zirconium salts are, for example, the product sold by the company Reheis under the name Reach AZP-908-SUF®, "activated" aluminium salts, for example the product sold by the company Reheis under the name Reach 103 or by the company Westwood under the name Westchlor 200.

Preferably, the cosmetic composition comprises aluminium chlorohydrate as antiperspirant active agent.

The antiperspirant aluminium salts may be present in the final composition according to the invention in a content ranging from 1% to 25% by weight, preferably in a content ranging from 2% to 20% and more particularly between 3% and 15% by weight relative to the total weight of the final composition.

Ethylenic Polymer

As indicated previously, the cosmetic composition comprises one or more water-insoluble film-forming block ethylenic polymers comprising a first block with a glass transition temperature (Tg) of greater than or equal to 85° C. and a second block with a Tg of less than or equal to 20° C. as defined after.

The term "ethylenic polymer" means a polymer obtained by polymerization of monomers comprising one or more ethylenic unsaturations.

The term "film-forming polymer" means a polymer that is capable of forming, by itself or in the presence of an auxiliary film-forming agent, a continuous film that adheres to a support, especially to keratin materials such as the skin, the hair, the eyelashes or the nails, especially the skin.

The term "water-insoluble polymer" means that the polymer is not soluble, according to the definition below.

The term "soluble polymer" means that the polymer dissolves in water or in a 50/50 by volume mixture of water and ethanol, or alternatively a mixture of water and isopropanol, without modification of the pH, at a solids content of 5% by weight, at room temperature (25° C., 1 atm.). The polymer is considered to be soluble if it does not form a precipitate or agglomerate that is visible to the naked eye when it is placed in solution, and if it therefore gives a clear solution.

Preferably, the polymer according to the invention is a polymer of linear or grafted structure. In contrast, a polymer of non-linear or ungrafted structure is, for example, a polymer of star or crosslinked structure.

The block ethylenic polymer according to the invention is preferentially prepared exclusively from monofunctional monomers. This means that the block ethylenic polymer does not contain any multifunctional monomers, which make it possible to break the linearity of a polymer so as to obtain in particular a crosslinked polymer, as a function of the content of multifunctional monomer.

Preferably, the polymer according to the invention is a non-elastomeric polymer, i.e. a polymer which, when it is subjected to a stress intended to stretch it (for example by 30% relative to its initial length), does not return to a length substantially identical to its initial length when the stress ceases.

More specifically, the term "non-elastomeric polymer" denotes a polymer with an instantaneous recovery Ri<50% and a delayed recovery $R_{2h}$<70% after having been subjected to a 30% elongation. Preferably, Ri is <30% and $R_{2h}$ is <50%.

The non-elastomeric nature of the polymer may be determined according to the following protocol: A polymer film is prepared by pouring a solution of the polymer in a Teflon-coated mould, followed by drying for 7 days in an environment conditioned at 23±5° C. and 50±10% relative humidity. A film about 100 µm thick is then obtained, from which are cut rectangular specimens (for example using a sample punch) 15 mm wide and 80 mm long. These specimen-shaped samples are subjected to a tensile stress using a machine sold under the reference Zwick, under the same temperature and humidity conditions as for the drying. The specimens are stretched at a speed of 50 mm/min and the distance between the jaws is 50 mm, which corresponds to the initial length (10) of the specimen.

The instantaneous recovery Ri is determined in the following manner:
 the specimen is stretched by 30% (ε max), i.e. approximately 0.3 times its initial length (10);
 the stress is removed by imposing a return speed equal to the tensile speed, i.e. 50 mm/minute, and the residual elongation of the specimen is measured as a percentage, after returning to zero stress (εi).

The instantaneous recovery Ri (as a percentage) is given by the formula below:

$$Ri = (\varepsilon\ max - \varepsilon i)/\varepsilon\ max \times 100$$

To determine the delayed recovery, the percentage residual elongation of the specimen (ε2h) is measured two hours after returning to zero stress. The delayed recovery $R_{2h}$ (as a percentage) is given by the following formula:

$$R_{2h} = (\varepsilon\ max - \varepsilon 2h)/\varepsilon\ max \times 100$$

The polymer according to the present invention is a block polymer, comprising a first block with a Tg of greater than or equal to 85° C. and a second block with a Tg of less than or equal to 20° C.

It is pointed out that the terms "first" and "second" blocks do not in any way condition the order of the said blocks in the structure of the polymer.

Preferably, the polymer comprises two distinct blocks (diblock) or, preferentially, three distinct blocks (triblocks).

Preferably, the said first and second blocks are mutually incompatible. The term "mutually incompatible blocks" means that the mixture formed from the polymer corresponding to the first block and from the polymer corresponding to the second block is not miscible in the polymerization solvent that is in major amount by weight of the block polymer, at room temperature (25° C.) and atmospheric pressure ($10^5$ Pa), for a content of the polymer mixture of greater than or equal to 5% by weight, relative to the total weight of the mixture (polymers and solvent), it being understood that:
 i) the said polymers are present in the mixture in a content such that the respective weight ratio ranges from 10/90 to 90/10, and that
 ii) each of the polymers corresponding to the first and second blocks has an average (weight-average or number-average) molecular mass equal to that of the block polymer±15%.

In the case of a mixture of polymerization solvents, and in the event that two or more solvents are present, the said polymer mixture is immiscible in at least one of them.

Needless to say, in the case of a polymerization performed in a single solvent, this solvent is the solvent that is in major amount.

The glass transition temperatures (Tg) indicated are, unless otherwise indicated, theoretical Tg values determined from the theoretical Tg values of the constituent monomers of each of the blocks, which may be found in a reference manual such as the Polymer Handbook, 4th Edition, (Brandrup, Immergut, Grulke), 1999, John Wiley, according to the following relationship, known as Fox's law:

$$\frac{1}{Tg} = \sum_i \left(\frac{wi}{Tgi}\right)$$

wi being the mass fraction of the monomer i in the block under consideration and Tgi being the glass transition temperature of the homopolymer of the monomer i (expressed in degrees Kelvin).

The polymer according to the invention thus comprises a block with a Tg of greater than or equal to 85° C., for example between 85 and 175° C., preferably between 90 and 150° C. and especially between 100 and 130° C.

The polymer according to the invention also comprises a block with a Tg of less than or equal to 20° C., for example between −100 and 20° C., preferably between −80 and 15° C. and especially between −60 and 10° C.

Preferably, the block with a Tg of greater than or equal to 85° C. represents 50% to 90% by weight and preferably 60% to 80% by weight relative to the weight of the final polymer.

Preferably, the block with a Tg of less than or equal to 20° C. represents 5% to 50% by weight and preferably 10% to 40% by weight relative to the weight of the final polymer.

Preferably, the said first and second blocks are linked together via an intermediate segment comprising at least one constituent monomer of the said first block and at least one constituent monomer of the said second block.

The intermediate segment is preferably a block comprising at least one constituent monomer of the first block and at least one constituent monomer of the second block of the polymer, allowing these blocks to be "compatibilized". The said intermediate segment or block is preferably a statistical copolymer.

Preferably, the said intermediate segment or block is derived essentially from constituent monomers of the first block and of the second block.

The term "essentially" means at least 85%, preferably at least 90%, better still 95% and even better still 100%.

Preferably, the said block ethylenic polymer has a polydispersity index Ip of greater than 2, especially between 2 and 9, preferably between 2.3 and 8 and better still between 2.4 and 7. The polydispersity index Ip is equal to the ratio of the weight-average molar mass Mw to the number-average molar mass Mn.

The weight-average molar mass (Mw) and number-average molar mass (Mn) are determined by gel permeation liquid chromatography (THF solvent, calibration curve established with linear polystyrene standards, UV and refractometric detector).

The weight-average molar mass (Mw) of the block ethylenic polymer is preferably between 35 000 and 300 000 and better still between 45 000 and 150 000 g/mol.

The number-average molar mass (Mn) of the block ethylenic polymer is preferably between 10 000 and 70 000 and better still between 12 000 and 50 000 g/mol.

Each block of the polymer according to the invention is derived from one type of monomer or from several different types of monomers. This means that each block may be a homopolymer or a copolymer, which may be statistical, alternating or of another form; preferably statistical. The chemical nature and/or the amount of the monomers constituting each of the blocks may obviously be chosen by a person skilled in the art, on the basis of his general knowledge, to obtain blocks having the required Tg values.

The block with a Tg of greater than or equal to 85° C., or first block, may thus be a homopolymer or a copolymer. It preferably comprises at least one monomer with a Tg of greater than or equal to 85° C.

When this block is a homopolymer, it may be derived from a monomer such that the homopolymer prepared from this monomer has a Tg of greater than or equal to 85° C.

When this block is a copolymer, it may be derived from one or more monomers whose nature and concentration are chosen such that the Tg of the resulting copolymer is greater than or equal to 85° C. The copolymer may comprise, for example, monomers which are such that the homopolymers prepared from these monomers have Tg values of greater than or equal to 85° C., for example a Tg ranging from 85 to 175° C., alone or as a mixture with monomers which are such that the homopolymers prepared from these monomers have Tg values of less than 85° C., preferably chosen from monomers with a Tg of between −100 and 85° C.

Similarly, the block with a Tg of less than or equal to 20° C., or second block, may be a homopolymer or a copolymer. It preferably comprises at least one monomer with a Tg of less than or equal to 20° C.

When this block is a homopolymer, it may be derived from a monomer such that the homopolymer prepared from this monomer has a Tg of less than or equal to 20° C.

When this block is a copolymer, it may be derived from one or more monomers whose nature and concentration are chosen such that the Tg of the resulting copolymer is less than or equal to 20° C. It may comprise, for example, monomers whose corresponding homopolymer has a Tg of less than or equal to 20° C., for example a Tg ranging from −100° C. to 20° C., alone or as a mixture with monomers whose corresponding homopolymer has a Tg of greater than 20° C., preferably chosen from monomers with a Tg of between 20 and 175° C.

The monomers whose homopolymer has a glass transition temperature (Tg) of greater than or equal to 85° C. (also known as monomers with a Tg of greater than or equal to 85° C.) may be chosen from the following monomers, alone or as a mixture:

the methacrylates of formula $CH_2=C(CH_3)-COOR_1$ in which $R_1$ represents a methyl or tert-butyl group; or a $C_6$ to $C_{12}$ cycloalkyl group such as isobornyl;

the acrylates of formula $CH_2=CH-COOR_2$ in which $R_2$ represents a $C_6$ to $C_{12}$ cycloalkyl group such as isobornyl, or a tert-butyl group;

the (meth)acrylamides of formula $CH_2=C(CH_3)-CONR_7R_8$ or $CH_2=CH-CONR_7R_8$, in which $R_7$ and $R_8$, which may be identical or different, represent a hydrogen atom or a methyl or isopropyl group; or $R_7$ represents H and $R_8$ represents a branched $C_3$ to $C_5$ group such as an isopropyl, sec-butyl, tert-butyl or 1-methylbutyl group; mention may be made of N-t-butylacrylamide, N-isopropylacrylamide and N,N-dimethylacrylamide;

styrene and derivatives thereof such as chlorostyrene.

Most particularly, mention may be made of methyl methacrylate, tert-butyl (meth)acrylate and isobornyl (meth)acrylate, and mixtures thereof.

The monomers whose homopolymer has a Tg of less than or equal to 20° C. may be chosen from the following monomers, alone or as a mixture:

the acrylates of formula $CH_2=CHCOOR_3$, with $R_3$ representing a linear or branched $C_1$ to $C_{12}$ alkyl group, with the exception of the tert-butyl group, in which one or more heteroatoms chosen from O, N and S are optionally intercalated, the said alkyl group also possibly being substituted with one or more substituents chosen from hydroxyl groups and halogen atoms (Cl, Br, I and F);

the methacrylates of formula $CH_2=C(CH_3)-COOR_4$, with $R_4$ representing a linear or branched $C_6$ to $C_{12}$ alkyl group in which one or more heteroatoms chosen from O, N and S are optionally intercalated, the said alkyl group also possibly being substituted with one or more substituents chosen from hydroxyl groups and halogen atoms (Cl, Br, I and F);

the vinyl esters of formula $R_5-CO-O-CH=CH_2$ in which $R_5$ represents a linear or branched $C_4$ to $C_{12}$ alkyl group;

$C_4$ to $C_{12}$ alkyl vinyl ethers, such as butyl vinyl ether and lauryl vinyl ether;

$N-(C_4-C_{12}$ alkyl)acrylamides, such as N-octylacrylamide.

Among the monomers with a Tg of less than or equal to 20° C., mention may also be made of the monomers of formula (I) below, alone or as a mixture:

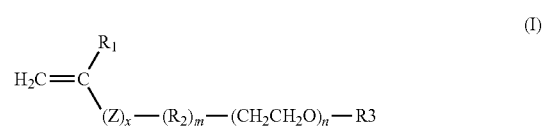

in which:

$R_1$ is a hydrogen atom or a methyl radical;

Z is a divalent group chosen from —COO—, —CONH—, —CONCH$_3$—, —OCO—, —O—, —SO$_2$— —CO—O—CO— and —CO—CH$_2$—CO—;

x is 0 or 1;

$R_2$ is a linear, branched or cyclic, saturated or unsaturated, optionally aromatic divalent carbon-based radical, of 1 to 30 carbon atoms, which may comprise 1 to 18 heteroatoms chosen from O, N, S, F, Si and P;

m is 0 or 1;

n is an integer between 3 and 300 inclusive;

$R_3$ is a hydrogen atom or a linear, branched or cyclic, saturated or unsaturated, optionally aromatic carbon-based radical, of 1 to 30 carbon atoms, which may comprise 1 to 20 heteroatoms chosen from O, N, S, F, Si and P.

Preferably, x=1 and Z represents COO or CONH, preferentially COO.

In the radical $R_2$, the heteroatom(s), when they are present, may be intercalated in the chain of the said radical $R_2$, or alternatively the said radical $R_2$ may be substituted with one or more groups comprising them such as hydroxyl, amino (NH$_2$, NHR' or NR'R" with R' and R", which may be identical or different, representing a linear or branched $C_1$-$C_{22}$ alkyl, especially methyl or ethyl), —CF$_3$, —CN, —SO$_3$H or —COOH.

In particular, $R_2$ may comprise a group —O—, —N(R)—, —CO— and a combination thereof, and especially —O—CO—O—, —CO—O—, —N(R)CO—; —O—CO—NR—, —NR—CO—NR—, with R representing H or a linear or branched $C_1$-$C_{22}$ alkyl, optionally comprising 1 to 12 heteroatoms chosen from O, N, S, F, Cl, Br, Si and P.

In particular, $R_2$ may be:
an alkylene radical containing 1 to 20 carbon atoms, such as methylene, ethylene, n-propylene, isopropylene, n-butylene, isobutylene, tert-butylene, pentylene, isopentylene, n-hexylene, isohexylene, heptylene, isoheptylene, n-octylene, isooctylene, nonylene, isononylene, decylene, isodecylene, n-dodecylene, isododecylene, tridecylene, n-tetradecylene, hexadecylene, n-octadecylene, docosanylene or arachinylene;
a substituted or unsubstituted cycloalkylene radical containing 5 to 10 carbon atoms, such as cyclopentylene, cyclohexylene, cycloheptylene, cyclooctylene, cyclononylene or cyclodecylene;
a phenylene radical —$C_6H_4$— (ortho, meta or para), optionally substituted with a $C_1$-$C_{12}$ alkyl radical optionally comprising 1 to 18 heteroatoms chosen from O, N, S, F, Si and P;
a benzylene radical —$C_6H_4$—$CH_2$— optionally substituted with a $C_1$-$C_{12}$ alkyl radical optionally comprising 1 to 18 heteroatoms chosen from O, N, S, F, Si and P;
a radical of formula —$CH_2$—O—CO—O—, $CH_2$—$CH_2$—O—CO—O—, —$CH_2$—CO—O—, —$CH_2$—$CH_2$—CO—O—, —$CH_2$—O—CO—NH—, —$CH_2$—$CH_2$—O—CO—NH—; —$CH_2$—NH—CO—NH—, —$CH_2$—$CH_2$—NH—CO—NH—; —$CH_2$—CHOH—, —$CH_2$—$CH_2$—CHOH—, —$CH_2$—$CH_2$—CH($NH_2$)—, —$CH_2$—$CH_2$—CH(NHR')—, —$CH_2$—$CH_2$—CH(NHR')—, —$CH_2$—$CH_2$—CH(NR'R")—, —$CH_2$—CH(NR'R")—, —$CH_2$—$CH_2$—$CH_2$—NR'—, —$CH_2$—$CH_2$—$CH_2$—O—; —$CH_2$—$CH_2$—CHR'—O— with R' and R" representing a linear or branched $C_1$-$C_{22}$ alkyl optionally comprising 1 to 12 heteroatoms chosen from O, N, S, F, Si and P;
or a mixture of these radicals.

Preferably, $R_2$ may be:
an alkylene radical containing 1 to 20 carbon atoms, especially methylene, ethylene, n-propylene, n-butylene, n-hexylene, n-octylene, n-dodecylene or n-octadecylene;
a phenylene radical —$C_6H_4$— (ortho, meta or para), optionally substituted with a $C_1$-$C_{12}$ alkyl radical optionally comprising 1 to 18 heteroatoms chosen from O, N, S, F, Si and P; or
a benzylene radical —$C_6H_4$—$CH_2$— optionally substituted with a $C_1$-$C_{12}$ alkyl radical optionally comprising 1 to 18 heteroatoms chosen from O, N, S, F, Si and P.

Preferably, n is between 5 and 200 inclusive, better still between 6 and 120 inclusive, or even between 7 and 50 inclusive.

Preferably, $R_3$ is a hydrogen atom; a phenyl radical optionally substituted with a $C_1$-$C_{12}$ alkyl radical optionally comprising 1 to 20 heteroatoms chosen from O, N, S, F, Si and P; a $C_1$-$C_{30}$, especially $C_1$-$C_{22}$ or even $C_2$-$C_{16}$ alkyl radical, optionally comprising 1 to 18 heteroatoms chosen from O, N, S, F, Si and P; a $C_3$-$C_{12}$, especially $C_4$-$C_8$ or even $C_5$-$C_6$ cycloalkyl radical, optionally comprising 1 to 18 heteroatoms chosen from O, N, S, F, Si and P.

Among the radicals $R_3$, mention may be made of methyl, ethyl, propyl, benzyl, ethylhexyl, lauryl, stearyl and behenyl (—$(CH_2)_{21}$—$CH_3$) chains, and also fluoroalkyl chains, for instance heptadecafluorooctyl sulfonyl amino ethyl $CF_3$—$(CF_2)_7$—$SO_2$—$N(C_2H_5)$—$CH_2$—$CH_2$; or alternatively —$CH_2$—$CH_2$—CN, succinimido, maleimido, mesityl, tosyl, triethoxysilane or phthalimide chains.

Preferentially, the monomers of formula (I) are such that:
x=1 and Z represents COO,
m=0,
n=6 to 120 inclusive,
$R_3$ is chosen from a hydrogen atom; a phenyl radical optionally substituted with a $C_1$-$C_{12}$ alkyl radical; a $C_1$-$C_{30}$, especially $C_1$-$C_{22}$ or even $C_2$-$C_{16}$ alkyl radical.

Preferably, the monomers of formula (I) have a molecular weight of between 300 and 5000 g/mol.

Among the monomers of formula (I) that are particularly preferred, mention may be made of:
poly(ethylene glycol) (meth)acrylate in which $R_1$ is H or methyl; Z is COO, x=1, m=0 and $R_3$=H;
methylpoly(ethylene glycol) (meth)acrylate, also known as methoxypoly(ethylene glycol) (meth)acrylate, in which $R_1$ is H or methyl; Z is COO, x=1, m=0 and $R_3$=methyl;
alkylpoly(ethylene glycol) (meth)acrylates in which $R_1$ is H or methyl; Z is COO, x=1, m=0 and $R_3$=alkyl;
phenylpoly(ethylene glycol) (meth)acrylates, also known as poly(ethylene glycol) (meth)acrylate phenyl ether, in which $R_1$ is H or methyl; Z is COO, x=1, m=0 and $R_3$=phenyl.

Examples of commercial monomers are:
CD 350 (methoxypoly(ethylene glycol 350) methacrylate) and CD 550 (methoxypoly(ethylene glycol 550) methacrylate), supplied by Sartomer Chemicals;
M90G (methoxypoly(ethylene glycol (9 repeating units)) methacrylate) and M230G (methoxypolyethylene glycol (23 repeating units) methacrylate) available from Shin-Nakamura Chemicals;
methoxypoly(ethylene glycol) methacrylates of average molecular weights 300, 475 or 1100, available from Sigma-Aldrich;
methoxypoly(ethylene glycol) acrylate of average molecular weight 426, available from Sigma-Aldrich;
the methoxypoly(ethylene glycol) methacrylates available from Laporte under the trade names: MPEG 350, MPEG 550, S10W and S20W, or from Cognis under the name Bisomer;
poly(ethylene glycol) monomethyl ether, mono(succinimidyl succinate) ester of average molecular weight 1900 or 5000, from Polysciences;
behenyl poly(ethylene glycol PEG-25) methacrylate, available from Rhodia under the name Sipomer BEM;
poly(ethylene glycol) phenyl ether acrylates of average molecular weights 236, 280 or 324, available from Aldrich;
methoxypolyethylene glycol 5000 2-(vinylsulfonyl) ethyl ether commercially available from Fluka;
polyethylene glycol ethyl ether methacrylate available from Aldrich;
polyethylene glycol 8000, 4000, 2000 methacrylates from Monomer & Polymer Dajac Laboratories;
methoxypoly(ethylene glycol) 2000 methacrylate Norsocryl 402 from Arkema;
methoxypoly(ethylene glycol) 5000 methacrylate Norsocryl 405 from Arkema;
poly(ethylene glycol) methyl ether acrylate from Aldrich, Mn=454 g/mol, DP=8-9.

Most particularly, among the monomers with a Tg of less than 20° C., mention may be made of alkyl acrylates in which the alkyl chain comprises from 1 to 10 carbon atoms, with the exception of the tert-butyl group, such as methyl acrylate, isobutyl acrylate and 2-ethylhexyl acrylate; and also poly(ethylene glycol) (meth)acrylates and alkylpoly(ethylene glycol) (meth)acrylates, more particularly methylpoly(ethylene glycol) methacrylates; and mixtures thereof.

The polymer according to the invention may also comprise additional monomers, which may be chosen, alone or as a mixture, from:
 ethylenically unsaturated monomers comprising at least one carboxylic or sulfonic acid function, for instance acrylic acid, methacrylic acid, crotonic acid, maleic anhydride, itaconic acid, fumaric acid, maleic acid, styrenesulfonic acid, acrylamidopropanesulfonic acid, vinylbenzoic acid or vinylphosphoric acid, and salts thereof,
 ethylenically unsaturated monomers comprising at least one hydroxyl function, for instance 2-hydroxypropyl methacrylate, 2-hydroxyethyl methacrylate, 2-hydroxypropyl acrylate or 2-hydroxyethyl acrylate,
 ethylenically unsaturated monomers comprising at least one tertiary amine function, for instance 2-vinylpyridine, 4-vinylpyridine, dimethylaminoethyl methacrylate, diethylaminoethyl methacrylate or dimethylaminopropylmethacrylamide, and salts thereof.

The block with a Tg of greater than or equal to 85° C. preferably comprises at least one acrylate monomer of formula $CH_2=CH-COOR$ and at least one methacrylate monomer of formula $CH_2=C(CH_3)-COOR$ in which R, which may be identical or different, represents a $C_4$ to $C_{12}$ cycloalkyl group and preferably a $C_8$ to $C_{12}$ cycloalkyl; preferably R is identical in the monomers; preferably, these monomers are isobornyl acrylate and methacrylate.

The acrylate monomer and the methacrylate monomer are preferably in mass proportions of between 30/70 and 70/30, preferably between 40/60 and 60/40 and especially of the order of 50/50.

The first block may be obtained exclusively from isobornyl acrylate and methacrylate, which are preferably in an acrylate/methacrylate mass proportion of between 30/70 and 70/30, preferably between 40/60 and 60/40 and especially of the order of 50/50.

The block with a Tg of less than or equal to 20° C. preferably comprises at least one monomer chosen, alone or as a mixture, from:
 the acrylates of formula $CH_2=CHCOOR_3$ in which $R_3$ represents a linear or branched $C_1$ to $C_{12}$ unsubstituted alkyl group, with the exception of the tert-butyl group, in which one or more heteroatoms chosen from O, N and S are optionally intercalated; especially isobutyl acrylate,
 the methacrylates of formula $CH_2=C(CH_3)-COOR_4$, in which $R_4$ represents a linear or branched $C_6$ to $C_{12}$ unsubstituted alkyl group, in which one or more heteroatoms chosen from O, N and S are optionally intercalated,
 (meth)acrylic acid;
 the monomers of formula (I), preferably with x=1 and Z=COO.

Preferentially, the block with a Tg of less than or equal to 20° C. comprises acrylic acid and/or methacrylic acid.

The block ethylenic polymer may be obtained by free-radical solution polymerization according to the following preparation process:
 part of the polymerization solvent may be introduced into a suitable reactor and heated until the adequate temperature for the polymerization is reached (typically between 60 and 120° C.),
 once this temperature has been reached, the constituent monomers of the first block may be added, in the presence of part of the polymerization initiator,
 after a time T corresponding to a maximum degree of conversion of preferably 90%, the constituent monomers of the second block and the rest of the initiator may be introduced,
 the mixture may be left to react for a time T' (ranging especially from 3 to 6 hours) after which the mixture is cooled to room temperature (25° C.), so as to obtain the polymer dissolved in the polymerization solvent.

The term "polymerization solvent" means a solvent or a mixture of solvents chosen especially from ethyl acetate, butyl acetate, $C_1$-$C_6$ alcohols such as isopropanol or ethanol, and aliphatic alkanes such as isododecane, and mixtures thereof. Preferably, the polymerization solvent is a mixture of butyl acetate and isopropanol or is isododecane.

The polymerization initiator may be chosen from organic peroxides comprising from 8 to 30 carbon atoms. An example that may be mentioned is 2,5-bis(2-ethylhexanoylperoxy)-2,5-dimethylhexane sold under the reference Trigonox® 141 by the company Akzo Nobel.

The block ethylenic polymer according to the invention is preferably prepared by free-radical polymerization and not by controlled or living polymerization. In particular, the polymerization is performed in the absence of control agents, and in particular in the absence of control agents conventionally used in living or controlled polymerization processes, such as nitroxides, alkoxyamines, dithioesters, dithiocarbamates, dithiocarbonates or xanthates, trithiocarbonates or copper-based catalysts, for example.

When it is present, the intermediate segment, or intermediate block, which connects the first block and the second block of the block polymer, may result from the polymerization of at least one monomer of the first block, which remains available after the polymerization to a maximum degree of conversion of 90% to form the first block, and of at least one monomer of the second block, added to the reaction mixture. The formation of the second block is initiated when the monomers of the first block no longer react or are no longer incorporated into the polymer chain either because they are all consumed or because their reactivity no longer allows them to be. Thus, the intermediate segment comprises the available monomers of the first block, resulting from a degree of conversion of these first monomers of less than or equal to 90%, during the introduction of the monomers of the second block during the synthesis of the polymer.

Among the block ethylenic polymers of the invention, use will more preferentially be made of a polymer chosen from:
 a poly(isobornyl acrylate/isobornyl methacrylate/isobutyl acrylate/acrylic acid) polymer,
 an isobornyl acrylate/isobornyl methacrylate/PEG methacrylate/acrylic acid statistical polymer and more particularly a poly(isobornyl acrylate/isobornyl methacrylate/isobutyl acrylate/acrylic acid) polymer.

The block ethylenic polymers according to the invention may be present in the final composition in a content ranging from 0.1% to 10% by weight of active material, preferably in a content ranging from 0.5% to 5% by weight and more preferentially in a content ranging from 0.8% to 3% by weight relative to the total weight of the final composition.

Oily Phase

The antiperspirant composition according to the invention comprises an oily phase, this phase containing at least one volatile oil.

Preferentially, the volatile oil is chosen from hydrocarbon-based volatile oils and silicone volatile oils, or mixtures thereof.

The term "oil" means a fatty substance which is liquid at room temperature (25° C.) and atmospheric pressure (760 mmHg, i.e. $10^5$ Pa). The oil may be volatile or non-volatile.

For the purposes of the invention, the term "volatile oil" means an oil that is capable of evaporating on contact with the skin or the keratin fibre in less than one hour, at room temperature and atmospheric pressure.

The volatile oils of the invention are volatile cosmetic oils which are liquid at room temperature and which have a non-zero vapour pressure, at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" means an oil that remains on the skin or the keratin fibre at room temperature and atmospheric pressure for at least several hours, and that especially has a vapour pressure strictly less than $10^{-3}$ mmHg (0.13 Pa).

The term "hydrocarbon-based oil" means an oil mainly containing carbon and hydrogen atoms and possibly one or more functions chosen from hydroxyl, ester, ether and carboxylic functions. Generally, the oil has a viscosity of from 0.5 to 100 000 mPa·s, preferably from 50 to 50 000 mPa·s and more preferably from 100 to 30 000 mPa·s.

Volatile Oils

As examples of volatile hydrocarbon-based oils that may be used in the invention, mention may be made of:

volatile hydrocarbon-based oils chosen from hydrocarbon-based oils containing from 8 to 16 carbon atoms, and in particular $C_8$-$C_{16}$ isoalkanes of petroleum origin (also known as isoparaffins), for instance isododecane (also known as 2,2,4,4,6-pentamethylheptane), isodecane and isohexadecane, and for example the oils sold under the trade names Isopar or Permethyl, branched $C_8$-$C_{16}$ esters and isohexyl neopentanoate, and mixtures thereof. Other volatile hydrocarbon-based oils, for instance petroleum distillates, especially those sold under the name Shell Solt by the company Shell, may also be used; volatile linear alkanes, such as those described in patent application DE10 2008 012 457 from the company Cognis.

As examples of volatile silicone oils that may be used in the invention, mention may be made of:

volatile linear or cyclic silicone oils, especially those with a viscosity ≤8 centistokes (8×$10^{-6}$ m²/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane;

volatile linear alkyltrisiloxane oils of general formula (I):

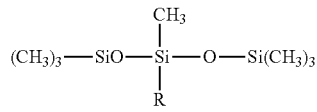

in which R represents an alkyl group comprising from 2 to 4 carbon atoms, one or more hydrogen atoms of which may be replaced with a fluorine or chlorine atom.

Among the oils of general formula (I), mention may be made of:
3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane, corresponding to the oils of formula (I) for which R is, respectively, a butyl group, a propyl group or an ethyl group.

The proportion of volatile oil(s) relative to the total amount of oils preferably ranges from 50% to 100% by weight.

Preferably, the volatile oils are chosen from hydrocarbon-based oils and more particularly $C_8$-$C_{16}$ isoalkanes such as isododecane or isohexadecane, or linear $C_8$-$C_{16}$ alkanes such as an undecane/tridecane mixture.

Even more particularly, isododecane will be chosen.

According to a particular form of the invention, the oily phase also comprises at least one non-volatile oil.

The non-volatile oils may be chosen from hydrocarbon-based oils, silicone oils and fluoro oils, and mixtures thereof.

Non-Volatile Hydrocarbon-Based Oils

As examples of non-volatile hydrocarbon-based oils that may be used in the invention, mention may be made of:

vegetable hydrocarbon-based oils, such as liquid triglycerides of fatty acids containing 4 to 24 carbon atoms, such as heptanoic or octanoic acid triglycerides, or else wheat germ oil, olive oil, sweet almond oil, palm oil, rapeseed oil, cottonseed oil, alfalfa oil, poppy seed oil, pumpkin seed oil, blackcurrant oil, evening primrose oil, millet oil, barley oil, quinoa oil, rye oil, safflower oil, candlenut oil, passionflower oil, musk rose oil, sunflower oil, maize oil, soybean oil, marrow oil, grape seed oil, sesame oil, hazelnut oil, apricot oil, macadamia oil, castor oil, avocado oil, caprylic/capric acid triglycerides, such as those sold by the company Stearineries Dubois or those sold under the names Miglyol 810, 812 and 818 by the company Dynamit Nobel, jojoba oil or shea butter oil;

linear or branched hydrocarbons of mineral or synthetic origin, such as liquid paraffins and derivatives thereof, petroleum jelly, polydecenes, polybutenes, hydrogenated polyisobutene, such as Parleam, or squalane;

synthetic ethers containing from 10 to 40 carbon atoms, such as dicaprylyl ether or PPG-14 butyl ether;

synthetic esters, in particular of fatty acids, for instance the oils of formula $R_1COOR_2$ in which $R_1$ represents the residue of a linear or branched higher fatty acid containing from 1 to 40 carbon atoms and $R_2$ represents a hydrocarbon-based chain, which is in particular branched, containing from 1 to 40 carbon atoms, with $R_1+R_2 \geq 10$, for instance purcellin oil (cetostearyl octanoate), isononyl isononanoate, isopropyl myristate, isopropyl palmitate, $C_{12}$ to $C_{15}$ alkyl benzoate, hexyl laurate, diisopropyl adipate, 2-ethylhexyl palmitate, 2-octyldodecyl stearate, 2-octyldodecyl erucate, isostearyl isostearate or tridecyl trimellitate; alcohol or polyalcohol octanoates, decanoates or ricinoleates, for instance propylene glycol dioctanoate; hydroxylated esters, for instance isostearyl lactate, octyl hydroxystearate, octyldodecyl hydroxystearate, diisostearyl malate, triisocetyl citrate, and fatty alcohol heptanoates, octanoates or decanoates; polyol esters, for instance propylene glycol dioctanoate, neopentyl glycol diheptanoate or diethylene glycol diisononanoate; and pentaerythritol esters, for instance pentaerythrityl tetraisostearate;

fatty alcohols that are liquid at room temperature, containing a branched and/or unsaturated carbon-based chain containing from 12 to 26 carbon atoms, for instance octyldodecanol, isostearyl alcohol, 2-butyloctanol, 2-hexyldecanol, 2-undecylpentadecanol or oleyl alcohol;

higher fatty acids such as oleic acid, linoleic acid or linolenic acid;

fatty-chain carbonates;

fatty-chain acetates;

fatty-chain citrates.

As examples of non-volatile silicone oils that may be used in the invention, mention may be made of:

silicone oils such as linear or cyclic non-volatile polydimethylsiloxanes (PDMSs); and mixtures thereof.

As examples of non-volatile fluoro oils that may be used in the invention, mention may be made of optionally partially hydrocarbon-based and/or silicone-based fluoro oils, such as fluorosilicone oils, fluorinated polyethers and fluorosilicones as described in document EP-A-847 752.

Preferably, the non-volatile oils will be chosen from non-volatile hydrocarbon-based oils and more particularly hydrogenated polyisobutene oils such as Parleam®, ethers such as dicaprylyl ether or PPG-14 butyl ether, fatty acid esters such as isopropyl palmitate, isononyl isononanoate or $C_{12}$-$C_{15}$ alkyl benzoates, fatty alcohols such as octyldodecanol, and mixtures thereof.

Fatty acid esters such as isopropyl palmitate, isononyl isononanoate or $C_{12}$-$C_{15}$ alkyl benzoates, and even more particularly isopropyl palmitate, will be chosen more preferentially.

The total amount of oil(s) present in the composition of the invention is preferably in a content ranging from 20% to 90% by weight and more preferentially in a content ranging from 30% to 80% by weight relative to the total weight of the liquid phase (or of the fluid).

For the purposes of the present invention, the term "liquid phase" or "fluid" means the base of the composition without the propellant.

For reasons of compatibility with the ethylenic polymer of the invention, when the oily phase of the composition comprises at least one non-volatile polydimethylsiloxane, the said phase must contain less than 15% by weight of non-volatile polydimethylsiloxane and more preferentially less than 12% by weight of non-volatile polydimethylsiloxane relative to the total weight of the oils.

Additives

The cosmetic compositions according to the invention may also comprise cosmetic adjuvants chosen from deodorant active agents, moisture absorbers, lipophilic suspension agents or gelling agents, softeners, antioxidants, opacifiers, stabilizers, moisturizers, vitamins, bactericides, preserving agents, polymers, fragrances, thickeners or suspension agents or any other ingredient usually used in cosmetics for this type of application.

Needless to say, a person skilled in the art will take care to select this or these optional additional compounds such that the advantageous properties intrinsically associated with the cosmetic composition in accordance with the invention are not, or are not substantially, adversely affected by the envisaged addition(s).

Deodorant Active Agents

According to a particular form of the invention, the compositions may contain at least one deodorant active agent in the liquid phase.

The term "deodorant active agent" is intended to mean any substance capable of reducing, masking or absorbing human body odours, in particular underarm odours.

The deodorant active agents may be bacteriostatic agents or bactericides that act on underarm odour microorganisms, such as 2,4,4'-trichloro-2'-hydroxydiphenyl ether (®Triclosan), 2,4-dichloro-2'-hydroxydiphenyl ether, 3',4',5'-trichlorosalicylanilide, 1-(3',4'-dichlorophenyl)-3-(4'-chlorophenyl)urea (®Triclocarban) or 3,7,11-trimethyldodeca-2,5,10-trienol (®Farnesol); quaternary ammonium salts such as cetyltrimethylammonium salts, cetylpyridinium salts, DPTA (1,3-diaminopropanetetraacetic acid), 1,2-decanediol (Symclariol from the company Symrise); glycerol derivatives, for instance caprylic/capric glycerides (Capmul MCM® from Abitec), glyceryl caprylate or caprate (Dermosoft GMCY® and Dermosoft GMC®, respectively from Straetmans), polyglyceryl-2 caprate (Dermosoft DGMC® from Straetmans), and biguanide derivatives, for instance polyhexamethylene biguanide salts; chlorhexidine and salts thereof; 4-phenyl-4,4-dimethyl-2-butanol (Symdeo MPP® from Symrise); zinc salts such as zinc salicylate, zinc gluconate, zinc pidolate, zinc sulfate, zinc chloride, zinc lactate or zinc phenolsulfonate; salicylic acid and derivatives thereof such as 5-n-octanoylsalicylic acid.

The deodorant active agents may be odour absorbers such as zinc ricinoleates or sodium bicarbonate; metallic or silver or silver-free zeolites, or cyclodextrins and derivatives thereof. They may also be chelating agents such as Dissolvine GL-47-S® from Akzo Nobel, EDTA and DPTA. They may also be a polyol such as glycerol or 1,3-propanediol (Zemea Propanediol sold by Dupont Tate and Lyle BioProducts); or also an enzyme inhibitor such as triethyl citrate; or alum.

The deodorant active agents may also be bacteriostatic agents or bactericides 2,4,4'-trichloro-2'-hydroxydiphenyl ether (Triclosan®), 2,4-dichloro-2'-hydroxydiphenyl ether, 3',4',5'-trichlorosalicylanilide, 1-(3',4'-dichlorophenyl)-3-(4'-chlorophenyl)urea (Triclocarban®) or 3,7,11-trimethyldodeca-2,5,10-trienol (Farnesol®); quaternary ammonium salts such as cetyltrimethylammonium salts or cetylpyridinium salts.

The deodorant active agents may be present in the composition according to the invention in a proportion from about 0.01% to 20% by weight relative to the total composition, and preferably in a proportion of from about 0.1% to 5% by weight relative to the total weight of the final composition.

Moisture Absorbers

It is also possible to add moisture absorbers, for instance perlites and preferably expanded perlites.

The cosmetic composition may comprise one or more moisture absorbers chosen from perlites.

Preferably, the cosmetic composition comprises one or more absorbers chosen from expanded perlites.

The perlites which can be used according to the invention are generally aluminosilicates of volcanic origin and have the composition:

70.0-75.0% by weight of silica $SiO_2$ 12.0-15.0% by weight of aluminium oxide $Al_2O_3$ 3.0-5.0% of sodium oxide $Na_2O$ 3.0-5.0% of potassium oxide $K_2O$ 0.5-2% of iron oxide $Fe_2O_3$ 0.2-0.7% of magnesium oxide $MgO$ 0.5-1.5% of calcium oxide $CaO$ 0.05-0.15% of titanium dioxide $TiO_2$ The perlite is ground, dried and then calibrated in a first stage. The product obtained, known as perlite ore, is grey-coloured and has a size of the order of 100 μm.

The perlite ore is subsequently expanded (1000° C./2 seconds) to give more or less white particles. When the temperature reaches 850-900° C., the water trapped in the structure of the material evaporates and brings about the expansion of the material, with respect to its original volume. The expanded perlite particles in accordance with the invention may be obtained via the expansion process described in U.S. Pat. No. 5,002,698.

Preferably, the perlite particles used will be ground; in this case, they are known as Expanded Milled Perlite (EMP). They preferably have a particle size defined by a median diameter D50 ranging from 0.5 to 50 μm and preferably from 0.5 to 40 μm.

Preferably, the perlite particles used have an untamped apparent density at 25° C. ranging from 10 to 400 $kg/m^3$ (standard DIN 53468) and preferably from 10 to 300 $kg/m^3$.

Preferably, the expanded perlite particles according to the invention have a water absorption capacity, measured at the wet point, ranging from 200% to 1500% and preferably from 250% to 800%.

The wet point corresponds to the amount of water which has to be added to 1 g of particle in order to obtain a homogeneous paste. This method derives directly from the oil uptake method applied to solvents.

The measurements are taken in the same manner by means of the wet point and the flow point, which have, respectively, the following definitions:

wet point: mass expressed in grams per 100 g of product corresponding to the production of a homogeneous paste during the addition of a solvent to a powder;

flow point: mass expressed in grams per 100 g of product above which the amount of solvent is greater than the capacity of the powder to retain it. This is reflected by the production of a more or less homogeneous mixture which flows over the glass plate.

The wet point and the flow point are measured according to the following protocol:

Protocol for Measuring the Water Absorption
1) Equipment Used
Glass plate (25×25 mm)
Spatula (wooden shaft and metal part, 15×2.7 mm)
Silk-bristled brush
Balance
2) Procedure The glass plate is placed on the balance and 1 g of perlite particles is weighed out. The beaker containing the solvent and the liquid sampling pipette is placed on the balance. The solvent is gradually added to the powder, the whole being regularly blended (every 3 to 4 drops) with the spatula.

The weight of solvent needed to obtain the wet point is noted. Further solvent is added and the weight which makes it possible to reach the flow point is noted. The average of three tests will be determined.

The expanded perlite particles sold under the trade names Optimat 1430 OR or Optimat 2550 by the company World Minerals will be used in particular.

Suspension Agents/Gelling Agents

The antiperspirant composition according to the invention may also contain one or more suspension agents and/or one or more gelling agents. Some of them may perform both functions simultaneously.

Among the agents that may be used as lipophilic suspension agents and/or gelling agents, mention may be made of clays, in powder form or in oily gel form, the said clays possibly being modified, especially modified montmorillonite clays such as hydrophobic-modified bentonites or hectorites, for instance hectorites modified with a $C_{10}$ to $C_{22}$ ammonium chloride, for instance hectorite modified with distearyldimethylammonium chloride, for instance the product disteardimonium hectorite (CTFA name) (product of reaction of hectorite and of distearyldimonium chloride) sold under the name Bentone 38 or Bentone Gel by the company Elementis Specialities. Mention may be made, for example, of the product Stearalkonium Bentonite (CTFA name) (product of reaction of bentonite and of quaternary stearalkonium ammonium chloride) such as the commercial product sold under the name Tixogel MP 250® by the company Sud Chemie Rheologicals, United Catalysts Inc.

Use may also be made of hydrotalcites, in particular hydrophobic-modified hydrotalcites, for instance the products sold under the name Gilugel by the company BK Giulini.

Mention may also be made of fumed silica optionally subjected to a hydrophobic surface treatment, the particle size of which is less than 1 μm. This is because it is possible to chemically modify the surface of the silica by chemical reaction which results in a decrease in the number of silanol groups present at the surface of the silica. Silanol groups can in particular be replaced by hydrophobic groups: a hydrophobic silica is then obtained. The hydrophobic groups can be trimethylsiloxyl groups, which are obtained in particular by treatment of fumed silica in the presence of hexamethyldisilazane. Silicas thus treated are named "silica silylate" according to the CTFA (8th edition, 2000). They are sold, for example, under the references Aerosil R812® by the company Degussa, Cab-O-Sil TS-530® by the company Cabot, dimethylsilyloxyl or polydimethylsiloxane groups, which are obtained especially by treating fumed silica in the presence of polydimethylsiloxane or dimethyldichlorosilane. Silicas thus treated are named "silica dimethyl silylate" according to the CTFA (8th Edition, 2000). They are sold, for example, under the references Aerosil R972® and Aerosil R974® by the company Degussa, and Cab-O-Sil TS-610® and Cab-O-Sil TS-720® by the company Cabot.

The hydrophobic fumed silica in particular has a particle size that may be nanometric to micrometric, for example ranging from about 5 to 200 nm.

According to a particular form of the invention, the suspension agents or gelling agents may be activated with oils such as propylene carbonate or triethyl citrate.

The amounts of these various constituents that may be present in the composition according to the invention are those conventionally used in compositions for treating perspiration.

Propellant

As indicated previously, the cosmetic composition comprises one or more propellants.

The propellant used in the antiperspirant cosmetic composition according to the invention is chosen from dimethyl ether, volatile hydrocarbons such as propane, isopropane, n-butane, isobutane, n-pentane and isopentane, and mixtures thereof, optionally with at least one chlorohydrocarbon and/or fluorohydrocarbon; among the latter, mention may be made of the compounds sold by the company DuPont de Nemours under the names Freon® and Dymel®, and in particular mono fluorotrichloromethane, difluorodichloromethane, tetrafluorodichloroethane and 1,1-difluoroethane sold especially under the trade name Dymel 152 A® by the company DuPont.

Carbon dioxide, nitrous oxide, nitrogen or compressed air may also be used as propellant.

Preferably, the antiperspirant cosmetic composition according to the invention comprises a propellant chosen from volatile hydrocarbons.

More preferentially, the propellant is chosen from isopropane, n-butane, isobutane, pentane and isopentane, and mixtures thereof.

The weight ratio between the liquid phase and the propellant gas varies in a ratio from 5/95 to 50/50, preferably from 10/90 to 40/60 and more preferentially from 15/85 to 30/70.

Preferably, the composition according to the invention comprises:

(i) an oily phase comprising, in a physiologically acceptable medium:
 one or more volatile oils chosen from hydrocarbon-based oils,
 one or more antiperspirant active agents chosen from aluminium salts,
 one or more water-insoluble film-forming block ethylenic polymers chosen from a poly(isobornyl acrylate/isobornyl methacrylate/isobutyl acrylate/acrylic acid) polymer, an isobornyl acrylate/isobornyl methacrylate/PEG methacrylate/acrylic acid statistical polymer, ii) one or more propellants.

The invention also relates to a cosmetic process for treating human perspiration, and optionally the body odours associated with human perspiration, which consists in applying to the surface of the skin an effective amount of the cosmetic composition as described previously.

The application time of the cosmetic composition on the surface of the skin may range from 0.5 to 10 seconds and preferably from 1 to 5 seconds.

The cosmetic composition in accordance with the invention may be applied several times to the surface of the skin.

In particular, the cosmetic treatment process according to the invention consists in applying to the surface of the armpits an effective amount of the cosmetic composition as described above.

The invention also relates to the use of the said composition for the cosmetic treatment of human perspiration.

Another subject of the present invention is an aerosol device consisting of a container comprising an aerosol composition as defined previously and of a means for dispensing the said composition.

The dispensing means, which forms a part of the aerosol device, generally consists of a dispensing valve controlled by a dispensing head, which itself comprises a nozzle via which the aerosol composition is vaporized. The container containing the pressurized composition may be opaque or transparent. It can be made of glass, of polymer or of metal, optionally covered with a protective lacquer layer.

The examples which follow illustrate the present invention without limiting the scope thereof.

The measurement of the transfer onto clothing was performed according to the protocol described below:

Each of the compositions to be studied was deposited on an imitation leather article sold under the name Supplale® by the company Idemitsu Technofine, which is bonded onto a smooth sheet weighing 170 g. This deposition is performed by spraying the aerosol for 2 seconds at a distance of 20 cm from the support.

After 24 hours, a black cotton fabric is placed on the imitation leather article. A 2 kg weight is then applied to the black fabric in order for the fabric to become impregnated with the composition.

The weight is moved to and fro over the entire length of the film while holding the fabric taut.

The fabric is scanned with a scanner sold under the name Epson V500 Scanner (16-bits grey setting, resolution 600 dpi).

The level of grey of the scans is then analysed using image software J which has a grey level ranging from 0 to 255. The higher the grey level value, the stronger the marks. It is thus sought to obtain the smallest possible grey level values.

The transfer evaluation is also performed by observation of the residual deposit on the synthetic leather plate:
 The persistence is considered as being very good when the deposit is unchanged after the fabric has been passed over
 It is considered as being good when the deposit is visible after the fabric has been passed over
 It is considered as being poor when the deposit is no longer (or only slightly) visible after the fabric has been passed over.

EXAMPLES

Example 1

1. Formulation

The formulations tested in aerosol form comprise a fluid manufactured according to the process described below and containing the ingredients mentioned in the following table:

| Phase | Ingredients | Fluid Invention Example 1 | Fluid Comparative C1 |
|---|---|---|---|
| A | Isopropyl palmitate | 4.29 | 12.29 |
| A | Isododecane | 32 | 40 |
| A | Acrylic acid/isobutyl acrylate/isobornyl acrylate copolymer (50% in isododecane)[1] | 16 | — |
| B | Disteardimonium hectorite[4] | 2.6 | 2.6 |
| C | Propylene carbonate[5] | 0.78 | 0.78 |
| D | Aluminium chlorohydrate[2] | 35 | 35 |
| D | Perlite[3] | 1.33 | 1.33 |
| E | Fragrance | 8 | 8 |

[1] sold under the trade name Mexomere PAS by the company Chimex
[2] sold under the trade name Reach 103 by the company Summitreheis
[3] sold under the trade name Optimat 2550 OR by the company World Minerals
[4] sold under the trade name Bentone 38VCG by the company Elementis
[5] sold under the trade name Jeffsol propylene carbonate by the company Huntsman Phase A is mixed with stirring. Phase (B) is introduced slowly into phase (A) and the mixture is then left to swell for 5 minutes. (C) is introduced. The mixture is stirred vigorously until good homogenization is obtained. The aluminium chlorohydrate and the perlite are then added portionwise. Stirring is continued to obtain good homogenization. The fragrance is then added.

The bases thus formulated are conditioned in cans and a propellant is added to the above preparations according to the following schemes:

|  | Invention Example 1 | Comparative C1 |
|---|---|---|
| Fluid Ex. 1 | 15 | — |

-continued

|  | Invention Example 1 | Comparative C1 |
|---|---|---|
| Fluid C1 | — | 15 |
| Isobutane | 85 | 85 |

2. Result Regarding the Transfer-Resistance Efficacy

The aerosol Example 1 is sprayed under the conditions described above and the results obtained comparative to the aerosol without Mexomere PAS® are described in the table below:

|  | Composition Example 1 | Composition Comparative C1 |
|---|---|---|
| Grey level of the fabric | 49.0 ± 2.2 | 72.8 ± 4.8 |
| Persistence of the deposit on synthetic leather | Good | Poor |

It is found that the composition of Example 1 (49.0) leaves fewer white marks on fabric, and makes it possible to obtain a more persistent deposit than composition C1 (72.8) not containing the polymer sold under the trade name Mexomere PAS.

Example 2

1. Formulation (Containing a Higher Concentration of Aluminium Chlorohydrate)

The formulations tested in aerosol form comprise a fluid manufactured according to the process described below and containing the ingredients mentioned in the following table:

| Phase | Ingredients | Fluid Invention Example 2 | Fluid Comparative C2 |
|---|---|---|---|
| A | Isopropyl palmitate | 10.88 | 15.88 |
| A | Isododecane | 24.74 | 29.74 |
| A | Acrylic acid/isobutyl acrylate/isobornyl acrylate copolymer (50% in isododecane)[1] | 10 | — |
| B | Disteardimonium hectorite[4] | 2.6 | 2.6 |
| C | Propylene carbonate[5] | 0.78 | 0.78 |
| D | Aluminium chlorohydrate[2] | 50 | 50 |
| D | Perlite[3] | 1 | 1 |

[1]sold under the trade name Mexomere PAS by the company Chimex
[2]sold under the trade name Reach 103 by the company Summitreheis
[3]sold under the trade name Optimat 2550 OR by the company World Minerals
[4]sold under the trade name Bentone 38VCG by the company Elementis
[5]sold under the trade name Jeffsol propylene carbonate by the company Huntsman Phase A is mixed with stirring. Phase (B) is introduced slowly into phase (A) and the mixture is then left to swell for 5 minutes. (C) is introduced. The mixture is stirred vigorously until good homogenization is obtained. The aluminium chlorohydrate and the perlite are then added portionwise in the form of a fine rain. Stirring is continued to obtain good homogenization.

The fluids (or bases) thus formulated are conditioned in cans and a propellant is added to the above preparations according to the following schemes:

|  | Invention Example 2 | Comparative C2 |
|---|---|---|
| Fluid Ex. 2 | 20 | — |
| Fluid C2 | — | 20 |
| Isobutane | 80 | 80 |

2. Result Regarding the Transfer-Resistance Efficacy

The aerosol Example 2 is sprayed under the conditions described above and the results obtained comparative to the aerosol without Mexomere PAS are described in the table below:

|  | Invention Example 2 | Comparative C2 |
|---|---|---|
| Grey level | 53.7 ± 0.4 | 84.4 ± 1.6 |
| Persistence of the deposit on synthetic leather | Good | Poor |

It is found that the composition Example 2 (53.7) leaves fewer white marks on fabric, and makes it possible to obtain a more persistent deposit than composition C1 (84.4) not containing the polymer sold under the trade name Mexomere PAS.

3. Antiperspirant Efficacy

The armpit evaluation is performed on a panel of 32 individuals for 4 days, according to the protocol described below:
- 21-day wash-out period without antiperspirant AP, with soap
- 1 armpit treated versus 1 armpit untreated
- 4 controlled applications: 1 application per day,
- Amount applied on each application: 1.2±0.05 g vaporized at a distance of 15 cm from the armpit
- Evaluation by gravimetry of the amount of sweat at T=0 and then 24 hours after the 4th application and 48 hours after the 4th application.

Measurement conditions:
Sweating in a sauna at 38° C. and relative humidity (RH)=30% to 40%
Sweating time: 1 h 20 mins (heating period: 40 minutes, then two 20-minute collection periods)

The antiperspirant efficacy measured for Example 2 is 30% after 24 hours and 25% after 48 hours.

Example 3

1. Formulation

The formulations tested in aerosol form comprise a fluid (or a base) manufactured according to the process described below and containing the ingredients mentioned in the following table:

| Phase | Ingredients | Fluid Invention Example 3 | Fluid Comparative C3 |
|---|---|---|---|
| A | Dimethicone[1] Percentage relative to the oils | 11 | 15 |

23

-continued

| Phase | Ingredients | Fluid Invention Example 3 | Fluid Comparative C3 |
|---|---|---|---|
| | Dimethicone[1] percentage relative to the total composition | 5.75 | 7.84 |
| A | Isododecane | 38.54 | 36.45 |
| A | Acrylic acid/isobutyl acrylate/isobornyl acrylate copolymer (50% in isododecane)[2] | 16 | 16 |
| B | Disteardimonium hectorite[5] | 2.6 | 2.6 |
| C | Propylene carbonate[6] | 0.78 | 0.78 |
| D | Aluminium chlorohydrate[3] | 35 | 35 |
| D | Perlite[4] | 1.33 | 1.33 |

[1]sold under the trade name Belsil DM 10 by the company Wacker
[2]sold under the trade name Mexomere PAS by the company Chimex
[3]sold under the trade name Reach 103 by the company Summitreheis
[4]sold under the trade name Optimat 2550 OR by the company World Minerals
[5]sold under the trade name Bentone 38VCG by the company Elementis
[6]sold under the trade name Jeffsol propylene carbonate by the company Huntsman Phase A is mixed with stirring. Phase (B) is introduced slowly into phase (A) and the mixture is then left to swell for 5 minutes. (C) is introduced. The mixture is stirred vigorously until good homogenization is obtained. The aluminium chlorohydrate and the perlite are then added portionwise. Stirring is continued to obtain good homogenization.

The fluids thus formulated are conditioned in cans and a propellant is added to the above preparations according to the following schemes:

| | Invention Example 3 | Comparative C3 |
|---|---|---|
| Fluid Example 3 | 15 | — |
| Fluid Comparative C3 | — | 15 |
| Isobutane | 85 | 85 |

2. Formulation Results

| | Invention Example 3 | Comparative C3 |
|---|---|---|
| Fluid | Homogeneous smooth opaque fluid | Mixing impossible, formation of a gum |
| Aerosol | Producible | Production impossible |

3. Result Regarding the Transfer-Resistance Efficacy

The aerosol Example 3 is sprayed under the conditions described above and the results obtained are described in the table below:

| | Invention Example 3 |
|---|---|
| Grey level on fabric | 49.2 ± 2.2 |

24

-continued

| | Invention Example 3 |
|---|---|
| Persistence of the deposit on artificial leather | Good |

The invention claimed is:

1. An anhydrous composition in aerosol form comprising:
i) a liquid phase comprising an oily phase comprising, in a physiologically acceptable medium:
at least one volatile oil,
at least one antiperspirant active agent chosen from aluminium and/or zirconium salts, and
at least one water-insoluble film-forming block ethylenic polymer comprising a first block with a glass transition temperature (Tg) of greater than or equal to about 85° C. and a second block with a Tg of less than or equal to about 20° C., and
ii) at least one propellant;
the oily phase containing less than about 11% by weight of non-volatile polydimethylsiloxane, relative to the total weight of the oils,
the second block comprising at least one monomer with a Tg of less than or equal to about 20° C., chosen from the following monomers, alone or as a mixture:
acrylates of formula $CH_2$=$CHCOOR_3$, wherein $R_3$ is chosen from a linear or branched $C_1$ to $C_{12}$ alkyl group, with the exception of the tert-butyl group, wherein at least one heteroatom chosen from O, N and S is optionally intercalated, the alkyl group optionally substituted with at least one substituent chosen from hydroxyl groups or halogen atoms;
methacrylates of formula $CH_2$=$C(CH_3)$—$COOR_4$, wherein $R_4$ is chosen from a linear or branched $C_6$ to $C_{12}$ alkyl group wherein at least one heteroatom chosen from O, N and S is optionally intercalated, the alkyl group optionally substituted with at least one substituent chosen from hydroxyl groups or halogen atoms;
vinyl esters of formula $R_5$—CO—O—CH=$CH_2$ in which $R_5$ is chosen from a linear or branched $C_4$ to $C_{12}$ alkyl group;
$C_4$ to $C_{12}$ alkyl vinyl ethers;
N—($C_4$ to $C_{12}$)alkyl acrylamides; or
monomers of formula (I) below, alone or as a mixture:

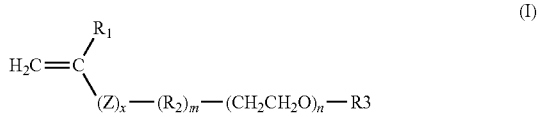

(I)

wherein:
$R_1$ is a hydrogen atom or a methyl radical;
Z is a divalent group chosen from —COO—, —CONH—, —CONCH$_3$—, —OCO—, —O—, —SO$_2$— —CO—O—CO—, or —CO—CH$_2$—CO—;
x is 0 or 1;
$R_2$ is a linear, branched or cyclic, saturated or unsaturated, optionally aromatic divalent carbon-based radical, of 1 to 30 carbon atoms, which may comprise 1 to 18 heteroatoms chosen from O, N, S, F, Si, and P;

m is 0 or 1;

n is an integer ranging from 3 to 300; and $R_3$ is a hydrogen atom or a linear, branched or cyclic, saturated or unsaturated, optionally aromatic carbon-based radical, of 1 to 30 carbon atoms, which may comprise 1 to 20 heteroatoms chosen from O, N, S, F, Si, and P;

wherein the anhydrous composition exhibits improved transfer-resistance compared to an anhydrous composition without the at least one water-insoluble film-forming block ethylenic polymer, as measured by grey level of a fabric when sprayed in aerosol form.

2. The composition according to claim 1, wherein the at least one antiperspirant agent chosen from aluminium salts are chosen from aluminium chlorohydrate, aluminium chlorohydrex, aluminium chlorohydrex PEG, aluminium chlorohydrex PG, aluminium dichlorohydrate, aluminium dichlorohydrex PEG, aluminium dichlorohydrex PG, aluminium sesquichlorohydrate, aluminium sesquichlorohydrex PEG, aluminium sesquichlorohydrex PG, alum salts, aluminium sulfate, aluminium zirconium octachlorohydrate, aluminium zirconium pentachlorohydrate, aluminium zirconium tetrachlorohydrate, or aluminium zirconium trichlorohydrate.

3. The composition according to claim 1, wherein the first and second blocks are linked together via an intermediate segment comprising at least one constituent monomer of the first block and at least one constituent monomer of the second block.

4. The composition according to claim 1, wherein the first block with a Tg of greater than or equal to about 85° C. comprises at least one monomer with a Tg of greater than or equal to about 85° C., chosen from the following monomers, alone or as a mixture:

methacrylates of formula $CH_2=C(CH_3)—COOR_1$ in which $R_1$ is chosen from a methyl or tert-butyl group, or a $C_6$ to $C_{12}$ cycloalkyl group;

acrylates of formula $CH_2=CH—COOR_2$ in which $R_2$ is chosen from a $C_6$ to $C_{12}$ cycloalkyl group or a tert-butyl group;

(meth)acrylamides of formula $CH_2=C(CH_3)—CONR_7R_8$ or $CH_2=CH—CONR_7R_8$, wherein $R_7$ and $R_8$, which may be identical or different, are chosen from a hydrogen atom or a methyl or isopropyl group; or $R_7$ represents H and $R_8$ represents a branched $C_3$ to $C_5$ group; or styrene, chlorostyrene, and derivatives thereof.

5. The composition according to claim 1, wherein the first block with a Tg of greater than or equal to about 85° C. comprises at least one monomer with a Tg of greater than or equal to about 85° C., chosen from methyl methacrylate, tert-butyl (meth)acrylate, isobornyl (meth)acrylate, or mixtures thereof.

6. The composition according to claim 1, wherein the second block with a Tg of less than or equal to about 20° C. of at least one water-insoluble film-forming block ethylenic polymer comprises at least one monomer with a Tg of less than or equal to about 20° C., chosen from methyl acrylate, isobutyl acrylate, 2-ethylhexyl acrylate, poly(ethylene glycol) (meth)acrylates, alkylpoly(ethylene glycol) (meth)acrylates, methylpoly(ethylene glycol) methacrylates, or mixtures thereof, with the exception of the tert-butyl group.

7. The composition according to claim 1, wherein the at least one water-insoluble film-forming block ethylenic polymer is chosen from:

a poly(isobornyl acrylate/isobornyl methacrylate/isobutyl acrylate/acrylic acid) polymer, or an isobornyl acrylate/isobornyl methacrylate/PEG methacrylate/acrylic acid statistical polymer.

8. The composition according to claim 1, wherein the at least one propellant is chosen from dimethyl ether, volatile hydrocarbons, n-butane, propane, isopropane, n-butane, isobutane, pentane, isopentane, or mixtures thereof, optionally with at least one chlorohydrocarbon and/or fluorohydrocarbon.

9. The composition according to claim 1, wherein the weight ratio between the liquid phase and the propellant gas ranges from about 5/95 to about 50/50.

10. The composition according to claim 1, wherein the weight ratio between the liquid phase and the propellant gas ranges from about 10/90 to about 40/60.

11. The composition according to claim 1, wherein the weight ratio between the liquid phase and the propellant gas ranges from about 15/85 to about 30/70.

12. The composition according to claim 1, wherein the at least one volatile oil is chosen from $C_8$-$C_{16}$ volatile hydrocarbon-based oils, $C_8$-$C_{16}$ isoalkanes, linear $C_8$-$C_{16}$ alkanes, or mixtures thereof.

13. The composition according to claim 12, wherein the at least one volatile oil is isododecane.

14. The composition according to claim 1, wherein the volatile oil is present in an amount ranging from about 50% to about 100% by weight, relative to the total amount of oil.

15. The composition according to claim 1, further comprising at least one moisture absorber chosen from perlites or expanded perlites.

16. A method for treating human perspiration, the method comprising applying to the surface of the skin an effective amount of the composition comprising:

i) an oily phase comprising, in a physiologically acceptable medium:

at least one volatile oil, at least one antiperspirant active agent chosen from aluminium and/or zirconium salts, and at least one water-insoluble film-forming block ethylenic polymer comprising a first block with a glass transition temperature (Tg) of greater than or equal to about 85° C. and a second block with a Tg of less than or equal to about 20° C., and ii) at least one propellant;

the oily phase containing less than about 11% by weight of non-volatile polydimethylsiloxane, relative to the total weight of the oils, the second block comprising at least one monomer with a Tg of less than or equal to about 20° C., chosen from the following monomers, alone or as a mixture:

acrylates of formula $CH_2=CHCOOR_3$, wherein $R_3$ is chosen from a linear or branched $C_1$ to $C_{12}$ alkyl group, with the exception of the tert-butyl group, wherein at least one heteroatom chosen from O, N and S is optionally intercalated, the alkyl group optionally substituted with at least one substituent chosen from hydroxyl groups or halogen atoms;

methacrylates of formula $CH_2=C(CH_3)—COOR_4$, wherein $R_4$ is chosen from a linear or branched $C_6$ to $C_{12}$ alkyl group wherein at least one heteroatom chosen from O, N and S is optionally intercalated, the alkyl group optionally substituted with at least one substituent chosen from hydroxyl groups or halogen atoms;

vinyl esters of formula $R_5$—CO—O—CH=$CH_2$ in which $R_5$ is chosen from a linear or branched $C_4$ to $C_{12}$ alkyl group;

$C_4$ to $C_{12}$ alkyl vinyl ethers;

N—($C_4$ to $C_{12}$)alkyl acrylamides; or monomers of formula (I) below, alone or as a mixture:

$$H_2C=C\begin{matrix}R_1\\ \\(Z)_x-(R_2)_m-(CH_2CH_2O)_n-R3\end{matrix} \qquad (I)$$

wherein:
$R_1$ is a hydrogen atom or a methyl radical;
Z is a divalent group chosen from —COO—, —CONH—, —CONCH$_3$—, —OCO—, —O—, —SO$_2$— —CO—O—CO—, or —CO—CH$_2$—CO—;
x is 0 or 1;
$R_2$ is a linear, branched or cyclic, saturated or unsaturated, optionally aromatic divalent carbon-based radical, of 1 to 30 carbon atoms, which may comprise 1 to 18 heteroatoms chosen from O, N, S, F, Si and P;
m is 0 or 1;
n is an integer ranging from 3 to 300; and
$R_3$ is a hydrogen atom or a linear, branched or cyclic, saturated or unsaturated, optionally aromatic carbon-based radical, of 1 to 30 carbon atoms, which may comprise 1 to 20 heteroatoms chosen from O, N, S, F, Si and P;
wherein the anhydrous composition exhibits improved transfer-resistance compared to an anhydrous composition without the at least one water-insoluble film-forming block ethylenic polymer, as measured by grey level of a fabric when sprayed in aerosol form.

17. A method for treating body odor associated with human perspiration, the method comprising applying to the surface of the skin an effective amount of the composition comprising:
i) an oily phase comprising, in a physiologically acceptable medium:
at least one volatile oil,
at least one antiperspirant active agent chosen from aluminium and/or zirconium salts, and
at least one water-insoluble film-forming block ethylenic polymer comprising a first block with a glass transition temperature (Tg) of greater than or equal to about 85° C. and a second block with a Tg of less than or equal to about 20° C., and
ii) at least one propellant;
the oily phase containing less than about 11% by weight of non-volatile polydimethylsiloxane, relative to the total weight of the oils,
the second block comprising at least one monomer with a Tg of less than or equal to about 20° C., chosen from the following monomers, alone or as a mixture:
acrylates of formula $CH_2$=CHCOOR$_3$, wherein $R_3$ is chosen from a linear or branched $C_1$ to $C_{12}$ alkyl group, with the exception of the tert-butyl group, wherein at least one heteroatom chosen from O, N and S is optionally intercalated, the alkyl group optionally substituted with at least one substituent chosen from hydroxyl groups or halogen atoms;

methacrylates of formula $CH_2$=C(CH$_3$)—COOR$_4$, wherein $R_4$ is chosen from a linear or branched $C_6$ to $C_{12}$ alkyl group wherein at least one heteroatom chosen from O, N and S is optionally intercalated, the alkyl group optionally substituted with at least one substituent chosen from hydroxyl groups or halogen atoms;

vinyl esters of formula $R_5$—CO—O—CH=$CH_2$ in which $R_5$ is chosen from a linear or branched $C_4$ to $C_{12}$ alkyl group;

$C_4$ to $C_{12}$ alkyl vinyl ethers;

N—($C_4$ to $C_{12}$)alkyl acrylamides; or monomers of formula (I) below, alone or as a mixture:

$$H_2C=C\begin{matrix}R_1\\ \\(Z)_x-(R_2)_m-(CH_2CH_2O)_n-R3\end{matrix} \qquad (I)$$

wherein:
$R_1$ is a hydrogen atom or a methyl radical;
Z is a divalent group chosen from —COO—, —CONH—, —CONCH$_3$—, —OCO—, —O—, —SO$_2$— —CO—O—CO—, or —CO—CH$_2$—CO—;
x is 0 or 1;
$R_2$ is a linear, branched or cyclic, saturated or unsaturated, optionally aromatic divalent carbon-based radical, of 1 to 30 carbon atoms, which may comprise 1 to 18 heteroatoms chosen from O, N, S, F, Si and P;
m is 0 or 1;
n is an integer ranging from 3 to 300; and
$R_3$ is a hydrogen atom or a linear, branched or cyclic, saturated or unsaturated, optionally aromatic carbon-based radical, of 1 to 30 carbon atoms, which may comprise 1 to 20 heteroatoms chosen from O, N, S, F, Si, and P;
wherein the anhydrous composition exhibits improved transfer-resistance compared to an anhydrous composition without the at least one water-insoluble film-forming block ethylenic polymer, as measured by grey level of a fabric when sprayed in aerosol form.

18. An aerosol device comprising:
a container comprising an aerosol composition comprising:
i) an oily phase comprising, in a physiologically acceptable medium:
at least one volatile oil,
at least one antiperspirant active agent chosen from aluminium and/or zirconium salts, and
at least one water-insoluble film-forming block ethylenic polymer comprising a first block with a glass transition temperature (Tg) of greater than or equal to about 85° C. and a second block with a Tg of less than or equal to about 20° C., and
ii) at least one propellant;
the oily phase containing less than about 11% by weight of non-volatile polydimethylsiloxane, relative to the total weight of the oils,
the second block comprising at least one monomer with a Tg of less than or equal to about 20° C., chosen from the following monomers, alone or as a mixture:

acrylates of formula $CH_2=CHCOOR_3$, wherein $R_3$ is chosen from a linear or branched $C_1$ to $C_{12}$ alkyl group, with the exception of the tert-butyl group, wherein at least one heteroatom chosen from O, N and S is optionally intercalated, the alkyl group optionally substituted with at least one substituent chosen from hydroxyl groups or halogen atoms;

methacrylates of formula $CH_2=C(CH_3)-COOR_4$, wherein $R_4$ is chosen from a linear or branched $C_6$ to $C_{12}$ alkyl group wherein at least one heteroatom chosen from O, N and S is optionally intercalated, the alkyl group optionally substituted with at least one substituent chosen from hydroxyl groups or halogen atoms;

vinyl esters of formula $R_5-CO-O-CH=CH_2$ in which $R_5$ is chosen from a linear or branched $C_4$ to $C_{12}$ alkyl group;

$C_4$ to $C_{12}$ alkyl vinyl ethers;

N—($C_4$ to $C_{12}$)alkyl acrylamides; or monomers of formula (I) below, alone or as a mixture:

$$H_2C=C\begin{matrix}R_1\\ (Z)_x-(R_2)_m-(CH_2CH_2O)_n-R3\end{matrix} \quad (I)$$

wherein:

$R_1$ is a hydrogen atom or a methyl radical;

Z is a divalent group chosen from —COO—, —CONH—, —CONCH$_3$—, —OCO—, —O—, —SO$_2$— —CO—O—CO—, or —CO—CH$_2$—CO—;

x is 0 or 1;

$R_2$ is a linear, branched or cyclic, saturated or unsaturated, optionally aromatic divalent carbon-based radical, of 1 to 30 carbon atoms, which may comprise 1 to 18 heteroatoms chosen from O, N, S, F, Si, and P;

m is 0 or 1;

n is an integer ranging from 3 to 300; and $R_3$ is a hydrogen atom or a linear, branched or cyclic, saturated or unsaturated, optionally aromatic carbon-based radical, of 1 to 30 carbon atoms, which may comprise 1 to 20 heteroatoms chosen from O, N, S, F, Si, and P;

wherein the anhydrous composition exhibits improved transfer-resistance compared to an anhydrous composition without the at least one water-insoluble film-forming block ethylenic polymer, as measured by grey level of a fabric when sprayed in aerosol form; and a dispenser for dispensing the aerosol composition.

* * * * *